(12) United States Patent
Patterson et al.

(10) Patent No.: US 9,757,354 B2
(45) Date of Patent: Sep. 12, 2017

(54) THERAPEUTIC FORMULATIONS AND METHODS

(71) Applicant: REGENTS OF THE UNIVERSITY OF MINNESOTA, Minneapolis, MN (US)

(72) Inventors: Steven Earl Patterson, Minneapolis, MN (US); Herbert Tsukasa Nagasawa, Minneapolis, MN (US); Robert Vince, Minneapolis, MN (US); Alexandre Monteil, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/177,150

(22) Filed: Jun. 8, 2016

(65) Prior Publication Data

US 2016/0354341 A1    Dec. 8, 2016

Related U.S. Application Data

(60) Provisional application No. 62/172,452, filed on Jun. 8, 2015.

(51) Int. Cl.
   *A61K 31/385*   (2006.01)
   *A61K 31/198*   (2006.01)
   *A61K 9/16*     (2006.01)
   *A61K 9/00*     (2006.01)

(52) U.S. Cl.
   CPC .......... *A61K 31/385* (2013.01); *A61K 9/0019* (2013.01); *A61K 9/16* (2013.01); *A61K 31/198* (2013.01)

(58) Field of Classification Search
   IPC ........................ A61K 31/385,31/198, 9/00, 9/16
   See application file for complete search history.

(56) References Cited

U.S. PATENT DOCUMENTS

| 5,834,448 A * | 11/1998 | Pouchol ............... A61K 9/0019 514/81 |
| 6,274,564 B1 * | 8/2001 | Sarill ................... A61K 31/685 514/52 |
| 2009/0197865 A1 | 8/2009 | Nagasawa et al. |
| 2012/0329731 A1 | 12/2012 | Nagasawa et al. |

FOREIGN PATENT DOCUMENTS

WO    WO 2011033893   * 10/2011

OTHER PUBLICATIONS

Brenner (Grants No. W81XWH-12-2-0098 (Sep. 26-Sep. 25, 2014).*
Brenner et al. Toxicol Appl Pharmacol. Nov. 1, 2010; 248(3): 269-276.*
Alarie, "Toxicity of Fire Smoke", Critical Reviews in Toxicology vol. 32 (4), 259-289 (2008).
Baskin, "In Vitro and In Vivo Comparison of Sulfur Donors as Antidotes to Acute Cyanide Intoxification", J. Appl. Toxicol., 19, 173-183 (1999).
Baud, et al., "Elevated blood cyanide concentrations in victims of smoke inhalation", The New England Journal of Medicine 325(25), 1761-1766 (1991).
Beaumont, et al., "Design of Ester Prodrugs to Enhance Oral Absorption of Poorly Permeable Compounds: Challenges to the Discovery Scientist", Current Drug Metabolism 4, 461-485 (2003).
Belani, et al., "Cyanide toxicity in juvenile pigs and its reversal by a new prodrug, sulfanegen sodium", Anesth Analg 114, 956-961 (2012).
Brenner, et al., "Sulfanegen sodium treatment in a rabbit model of sub-lethal cyanide toxicity", Toxicol Appl Pharmacol 248, 269-276 (2010).
Cavallini, "The Oxidation of Sulfur-Containing Amino Acids by L-Amino Acid Oxidases", Advances in Experimental Medicine and Biology, 148, 359-374, (1982).
Chan, et al., "The combination of cobinamide and sulfanegen is highly effective in mouse models of cyanide poisoning", Clin Toxicol 49(5), 16 pp. (2011).
Clemedson, "On the Toxicity of Sodium beta-mercapto pyruvate and Its Antidotal Effect against Cyanide", Acta. Physiol. Scand. 42, 41-45, (1958).
Cooper, "On the Chemistry and Biochemistry of 3-Mercaptopyruvic Acid, the □-Keto Acid Analog of Cysteine", J. Biol. Chem., 257, 816-826, (1982).
Crankshaw, et al., "A novel paradigm for assessing efficacies of potential antidotes against neurotoxins in mice", Toxicol Lett 175, 111-117 (2007).
Esposito, et al., "Inhalation toxicity of carbon monoxide and hydrogen cyanide gases released during thermal decomposition of polymers", J Fire Sci 6, 195-242 (1988).
Huang, et al., "Hepatocyte-Catalysed Detoxification of Cyanide by L- and D-Cysteine", Biochemical Pharmacology, vol. 55, 1983-1990 (1998).
Jarabak, "3-Mercaptopyruate Sulfurtransferase (Rhodanese)", Methods in Enzymology, Academic Press (Jakoby, W.B., Ed.), vol. 77, 291-297 (1981).
Koplovitz, "Assessment of Motor Performance Decrement Following Soman Poisoning in Mice", Drug and Chemical Toxicology, 12, 221-235 (1989).
Meister, "Enzymatic Desulfurization of Mercaptopyruvate to Pyruvate", Journal of Biological Chemistry, 206, 561-575 (1954).
Mousa, et al., "Alternative Sulphur Donors for Detoxification of Cyanide in the Chicken", Comp Biochem Physiol vol. 99C(3), 309-315 (1991).
Nagahara, et al., "Do antidotes for acute cyanide poisoning act on mercaptopyruvate sulfurtransferase to facilitate detoxification?", Curr Drug Targets Immune Endocr Metabol Disord 3, 198-204 (2003).
Nagasawa, et al., "Novel, Orally Effective Cyanide Antidotes", J Med Chem 50, 6462-6464 (2007).
Patterson, et al., "Cyanide antidotes for mass casualties: water-soluble salts of the dithiane (sulfanegen) from 3-mercaptopyruvate for intramuscular administration", J Med Chem 56, 1346-1349 (2013).
Schubert, et al., "Antagonism of Experimental Cyanide Toxicity in Relation to the In Vivo Activity of Cytochrome Oxidase", Journal of Pharmacology and Experimental Therapeutics vol. 162(2), 352-359 (1968).

(Continued)

Primary Examiner — Shirley V Gembeh
(74) Attorney, Agent, or Firm — Viknins Harris Padys Malen LLP

(57) ABSTRACT

The invention provides compositions and methods for treating cyanide poisoning.

23 Claims, 2 Drawing Sheets

(56) References Cited

OTHER PUBLICATIONS

Scifinder, CAS Registry No. 80003-64-1, American Chemical Society (ACS), 2 pages. (2013).
Singh, et al., "Stylet-Assisted Tracheal Intubation Through an ILMA in a Patients with an Anterior Larynx", Anesthesiology and Analgesia vol. 115 (2), 480-481 (2012).
Tanabe, "Preparation of a Sulfurtransferase Substrate, Sodium 3-Mercaptopyruvate, from 3-Bromopyruvic acid and Sodium Hydrosulfide", Chem. Pharm. Bull., 37, 2843-2845 (1989).
Testa, "Prodrug research: futile or fertile?", Biochemical Pharmacology 68, 2097-2106 (2004).
Tulsawani, "Effect of sub-acute oral cyanide administration in rats: Protective efficacy of alpha-ketoglutarate and sodium thiosulfate", Chemico-Biological Interactions, 156, 1-12, (2005).
Way, "Cyanide Antagonism with Mercaptopyruvate", Federation Proceedings 44(3), 1797 (1985).
Westley, "Rhodanse and the Sulfane Pool", Enzymatic Basis of Detoxification, vol. 2, Jakoby, W.B. Ed., 245-259 (1980).
Westley, "Thiosulfate: Cyanide Sulfurtransferase (Rhodanese)", Methods in Enzymology, Academic Press, Jakoby, W.B. Ed., 77, 285-291 (1981).
Wolff, "Burger's Medicinal Chemistry and Drug Discovery", Fifth Edition, vol. 1: Principles and Practice, 975-977 (1995).

\* cited by examiner

THERAPEUTIC FORMULATIONS AND METHODS

CROSS-REFERENCE TO RELATED APPLICATIONS

This patent application claims the benefit of priority of U.S. application Ser. No. 62/172,452, filed 8 Jun. 2015, which application is herein incorporated by reference.

GOVERNMENT FUNDING

This invention was made with government support under U01NS058087-06 awarded by the National Institutes of Health. The government has certain rights in the invention.

BACKGROUND OF THE INVENTION

Cyanide is widely regarded an archetypal poison. In the United States, industrial use exceeds 1 billion pounds yearly in diverse areas including electroplating, plastics and gold extraction. Dzomback, D. A., et al., *Cyanide in Water and Soil: Chemistry, Risk and Management*. CRC Press: Boca Raton, Fla., 2006.

Cyanide salts are relatively easy to prepare and release hydrogen cyanide from simple reagents. The risk of mass casualties from an industrial accident is highlighted by the Bhopal disaster in 1984 and in terrorist plots to release chemical agents including cyanide in the subways of Tokyo in 1995, Chicago in 2002 and New York in 2003. Additionally, cyanide is also released during combustion of nitrogenous materials and, in addition to carbon monoxide, is a major factor in fatalities by smoke inhalation. Lecarpentier, Y., et al., *N. Engl. J. Med.* 1991, 325, 1761-1766; Esposito, F. M.; Alarie, Y., *J. Fire Sci.* 1988, 6, 195-242; and Alarie, Y., *Crit. Rev. Toxicol.* 2002, 32, 259-289.

The currently available cyanide antidotes in the U.S. are hydroxocobalamin (Cyanokit) and the combination of sodium nitrite and sodium thiosulfate (Nithiodote). Both these treatments are limited in that they must be administered intravenously (iv) over a period of 5-15 min. The need to establish an iv line and the slow infusion rates required render these agents unsuitable for a mass casualty setting. Development of an antidote suitable for rapid intramuscular (im) administration should address the above concerns; however, this requires an antidote that can be delivered in a small volume for rapid absorption.

There are two pathways in mammals that detoxify cyanide as thiocyanate: rhodanese (thiosulfate/cyanide sulfur transferase EC 2.8.1.2) and 3-mercaptopyruvate sulfurtransferase (3-MST, EC 2.8.1.1). While the rhodanse pathway is currently exploited clinically with sodium thiosulfate, 3-MST should be a more efficient pathway in that 3-MST is more widely distributed in tissues, including the central nervous system than rhodanese. Additionally, 3-MST is present in the cytosol as well as in mitochondria whereas rhodanese is concentrated solely in the mitochondria. The endogenous substrate for 3-MST is the deaminated cysteine catabolite, 3-mercaptopyruvate (3-MP, 1) however the poor stability of 3-MP renders this substrate a poor drug candidate. Nagahara, N., et al., *Curr. Drug Targets Immune Endocr. Metabol. Disord.* 2003, 3, 198-204. Thus, some efforts have focused on developing prodrugs of 3-MP. Nagasawa, H. T., et al., *J. Med. Chem.* 2007, 50, 6462-6464; Patterson, S. E., et al., *J. Med. Chem.* 2013, 56, 1346-1349; Singh, H., et al., *Anesthesiology and Analgesia* 2012, in press; Chan, A., et al., *Clin. Toxicol. (Phila.)* 2011, 49, 366-373; and Brenner, M., et al., *Toxicol. Appl. Pharmacol.* 2010, 248, 269-276.

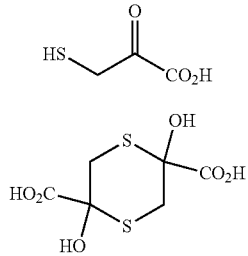

3-Mercaptopyruvic acid (1,3-MP), the endogenous substrate for 3-MST and its dithiane form (2).

The dithiane form of 3-MP (sulfanegenic acid, 2), as a sodium salt (sulfanegen sodium, 3a) is highly effective in rescue of our sublethal murine and lethal swine models of cyanide toxicity when administered intraperitoneally (ip) and iv. Nagasawa, H. T., et al., *J. Med. Chem.* 2007, 50, 6462-6464; Belani, K. G., et al., *Anesth. Analg.* 2012, 114, 956-961; and Crankshaw, D. L., et al., *Toxicol. Lett.* 2007, 175, 111-117. Based on a 60 kg human with a maximum injectable volume of 5 mL dose, calculations revealed that minimal water solubility of 1.05 M was required for effective im administration. However, the aqueous solubility of sulfanegen sodium, 3a, is 0.35 M; hence 3a is not optimal for development as an im cyanide antidote.

Additionally, sulfanegen triethanolamine has been investigated for preclinical development. Patterson, S. E., et al., *J. Med. Chem.* 2013, 56, 1346-1349. Unfortunately, it has been determined that this sulfanegen salt has poor thermal stability with a short (<6 month) shelf life at room temperature (unpublished results). Accordingly, there is currently a need for a sulfanegen formulation that is well tolerated, has acceptable thermal stability, and is effective in lethal models of cyanide toxicity. Ideally, the formulation will be suitable for im administration.

SUMMARY OF THE INVENTION

Efforts in developing an improved treatment for cyanide-exposed victims have focused on 1) improving the efficiency of the endogenous cyanide detoxification pathways by supplying a substrate in prodrug form, and 2) development of the prodrug in a form amenable to rapid administration by the im route. A sulfanegen formulation that is well tolerated, has acceptable thermal stability, and is effective in lethal models of cyanide toxicity has been identified.

Accordingly, in one embodiment the invention provides a composition comprising: sulfanegen lysine, lysine hydrochloride, and water.

In one embodiment, the invention provides a pharmaceutical composition prepared by combining sulfanegen lysine, lysine hydrochloride, and water.

In one embodiment, the invention provides a pharmaceutical composition prepared by combining sulfanegenic acid and a solution of lysine in water.

In one embodiment, the invention provides a pharmaceutical composition prepared by combining sulfanegenic acid and a solution prepared by combining water, lysine and lysine hydrochloride.

In one embodiment, the invention provides a composition comprising sulfanegenic acid solid (e.g., powder), lysine solid (e.g., powder), and lysine hydrochloride solid (e.g., powder).

In one embodiment, the invention provides a composition prepared by combining sulfanegenic acid solid (e.g., powder), lysine solid (e.g., powder), and lysine hydrochloride solid (e.g., powder).

In one embodiment, the invention provides a method comprising combining a) a solution prepared by combining water, lysine and lysine hydrochloride and b) sulfanegenic acid (e.g., sulfanegenic acid solid (e.g., powder)) to provide a resulting solution.

In one embodiment, the invention provides a method comprising combining a) water and b) sulfanegenic acid solid (e.g., powder), lysine solid (e.g., powder), and lysine hydrochloride solid (e.g., powder) to provide a resulting solution.

In one embodiment, the invention provides a kit comprising a) a solution prepared by combining water, lysine and lysine hydrochloride; b) sulfanegenic acid solid (e.g., powder); and instructions for combining the solution and the solid (e.g., powder) to provide a composition suitable for treating cyanide poisoning.

In one embodiment, the invention provides a kit comprising a) sulfanegenic acid solid (e.g., powder), lysine solid (e.g., powder), and lysine hydrochloride solid (e.g., powder); and instructions for combining the sulfanegenic acid solid (e.g., powder), lysine solid (e.g., powder), and lysine hydrochloride solid (e.g., powder) with water to provide a composition suitable for treating cyanide poisoning.

In one embodiment, the invention provides a composition as described herein for the prophylactic or therapeutic treatment of cyanide poisoning.

In one embodiment, the invention provides the use of a composition as described herein for treating cyanide poisoning in an animal (e.g., a mammal such as a human).

In one embodiment, the invention provides a method further comprising administering the resulting solution to an animal (e.g., a mammal such as a human).

DETAILED DESCRIPTION

Figure 1:
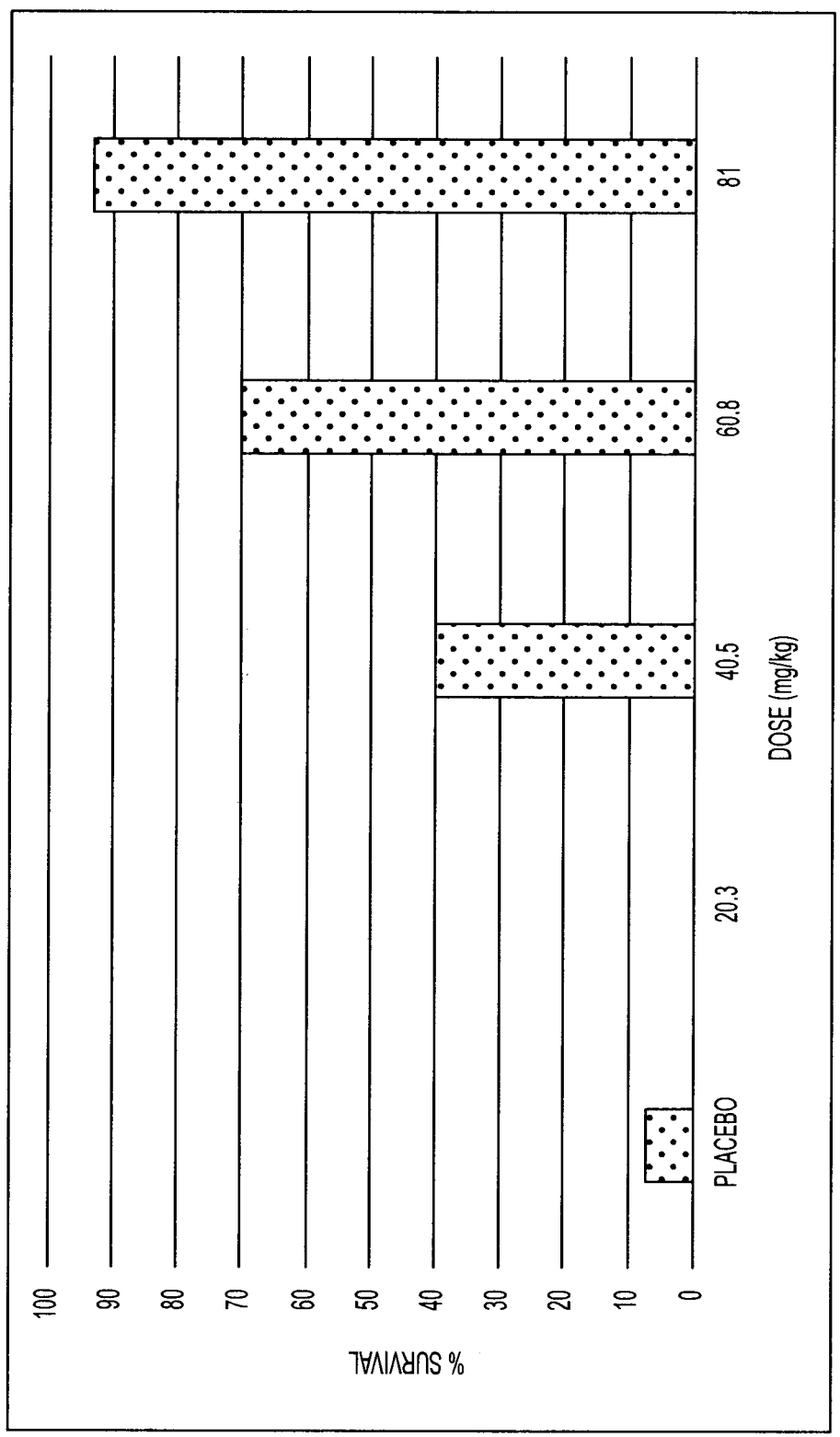
FIG. 1 shows the dose response of sulfanegen lysine in the murine cyanide toxicity model. Percent survival on the vertical axis and dose of the sulfanegen lysine/lysine HCl formulation equivalent to free sulfanegenic acid or placebo (phosphate buffered saline) on the horizontal axis (Example 1).

The term "effective amount" refers to the dose required to reduce or eliminate one or more of the symptoms of cyanide poisoning.

The term combating cyanide poisoning includes prophylactic use as well as treatment of a subject that has already been exposed to cyanide.

The present salts may be administered, e.g., im, iv, io, or po (orally), in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should generally contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously (iv), intraperitoneally (ip), intraosseously (io), or intramuscularly (im) by infusion or injection, e.g., using an autoinjector. The compounds may be administered using an autoinjector. Solutions of the active compound can be prepared in water, optionally mixed with a nontoxic surfactant. Dispersions can also be prepared in glycerol, liquid polyethylene glycols, triacetin, and mixtures thereof and in oils. The active compounds can also be formulated as nanoparticle suspensions. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of a compound required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as a cyanide antidote may be determined using pharmacological models which are well known to the art, or using the models described in the Examples below.

The invention will now be illustrated by the following non-limiting Examples.

Example 1

Metal salts other than sodium were prepared via ion exchange chromatography from sodium salt 3a as described in Example 2. Using methods previously described (Patterson, S. E., et al., *J. Med. Chem.* 2013, 56, 1346-1349) a library of sulfanegenic acid salts was also prepared using biocompatible amines and amino acids. While the lithium salt gave improvement over the sodium salt in solubility (1.05 M vs 0.35 M) other salts were investigated due to concerns over the tolerability of lithium. Singh, L. K., et al., *Am. J. Ther* 2011, 18, 288-291. The solubility of a number of prepared sulfanegenic acid salts is shown in Table 1.

TABLE 1

Solubility of sulfanegen metal salts and ammonium salts.

| Compound | Counterion | Solubility (M @ 20° C.) |
|---|---|---|
| 2 | 2H+ | 0.20 |
| 3a | 2 Na+ | 0.35 |
| 3b | 2 Li+ | 1.05 |
| 3c | 2 K+ | 0.57 |

TABLE 1-continued

Solubility of sulfanegen metal salts and ammonium salts.

| Compound | Counterion | Solubility (M @ 20° C.) |
|---|---|---|
| 3d | 2 Cs+ | 0.40 |
| 3e | 2 NH$_4^+$ | 0.16 |
| 3f | Ca$^{2+}$ | <0.1 |
| 3g | H$_3$N+–CH$_2$CH$_2$–NH$_3$+ | 0.02 |
| 3h | 2 [CH$_3$CH$_2$–NH$_2^+$–CH$_2$CH$_3$] | 2.26 |
| 3i | 2 L-His | 0.14 |
| 3j | 2 D-Lys | 1.05 |
| 3k | 2 L-Lys | 0.98 |
| 3l | 2 L-Asp | 0.05 |
| 3m | 2 L-Glu | 0.07 |
| 3n | 2 L-Ser | 1.00 |
| 3o | 2 L-Thr | 0.48 |
| 3p | 2 L-Asn | 0.27 |
| 3q | 2 L-Gln | 0.24 |
| 3r | 2 L-Gly | 0.10 |
| 3s | 2 L-Pro | 0.13 |
| 3f | 2 L-Ala | 0.36 |
| 3u | 2 L-Val | 0.21 |
| 3v | 2 L-Ile | 0.17 |
| 3w | 2 L-Leu | 0.10 |
| 3x | 2 L-Met | 0.23 |
| 3y | 2 L-Phe | 0.13 |
| 3z | 2 L-Trp | 0.12 |
| 3aa | 2 Creatine | 0.21 |
| 3bb | 2 L-Carnitine | 0.28 |
| 3cc | 2 Ornithine | 0.34 |
| 3dd | 2 [H$_3$N+–CH(CH$_2$NH$_3^+$)–C(=O)–O$^-$] | 0.17 |

During characterization of these ammonium salts, a relatively rapid decomposition of the sulfanegen pharmacophore was observed for all of the salts with simple amines. In most cases, this was evident by the discoloration of the aqueous solutions within about 15 minutes of dissolution. In addition, none of the salts prepared from the amines were stable on storage for more than 6 months even as a dry powder at room temperature, whereas in similar storage conditions the free acid was stable for greater than 3 years.

Unexpectedly, the salt prepared from lysine was stable in solution for at least 24 hours. This salt was also highly soluble (1.05 M) and stable when stored as a dry powder for at least one year. Moreover, the salts prepared from the other diamino acids 2,3-diaminopropionic acid and ornithine were far less soluble than the lysine salt (0.17 M and 0.34 M respectively).

Accordingly, the lysine salt was selected for further development. Because the lysine salt had poor long term solution stability, its use as a cyanide antidote required dissolution just prior to administration. Initial efforts at simply dissolving the salts in water gave unsatisfactory results. While the salt is highly soluble (>1.0 M), in most cases complete dissolution to achieve a saturated solution required vigorous shaking for more than 1 minute. In order to speed dissolution, generation of the desired salt in situ was investigated. A concentrated (2 M or greater) aqueous solution of lysine was added to a stoichiometric amount the free acid 2. This resulted in rapid formation of a solution of the bis-lysine salt of sulfanegenic acid, and complete dissolution was achieved in less than 20 seconds. Further investigation revealed that this method appeared to be general. Addition of an aqueous deanol, or triethanolamine solution to sulfanegenic acid led to rapid dissolution and in situ formation of the respective salts.

Attempts at further optimization of the lysine salt revealed that while sub-stoichiometric amounts of lysine gave improved solution stability, dissolution was less rapid. Additionally, the use of sub-stoichiometric amounts of lysine resulted in pH of the resulting solutions below 4. Injection of such acidic solutions were poorly tolerated in a rabbit model, resulting in poor absorption of the antidote. Investigations of the effect of pH on the stability of sulfanegen sodium (3a) revealed that at pH>5 a slow decomposition was observed. At pH>8 the salt 3a decomposed rapidly. Therefore, the optimal pH for the resulting salts of sulfanegenic acid is between 4 and 5.

The buffering action of lysine hydrochloride was also investigated to further stabilize the sulfanegen pharmacophore. For the lysine salt, optimal results for dissolution rate, pH, and stability were achieved when sulfanegenic acid was dissolved with a solution containing 2 equivalents of lysine and 0.4 equivalent of lysine hydrochloride.

Antidotal efficacy was studied in lethal murine and rabbit models of cyanide toxicity. Because the ethical guidelines of our Institutional Animal Care and Use Committee (IACUC) require anesthesia for lethal animal models, all our animals were anesthetized for the efficacy experiments. The mouse model: anesthetized Swiss-Webster mice (2% isoflurane/room air in a chamber at 36° C.) received KCN (ip, 0.16 mmol/kg in phosphate buffered saline) followed by the sulfanegenic acid salt or placebo (phosphate buffered saline) 60 seconds later (im, gastrocnemius muscle) with death/survival as the endpoint.

The rabbit model: New Zealand white (NZW) rabbits were sedated (telazol, im) before general anesthesia with isoflurane (3% in room air), and kept normocarbic and normothermic with a forced air warming device (Arizant Inc., Eden Prairie, Minn.). Using sterile techniques, a catheter was placed percutaneously (ear lobe) for continuous blood pressure monitoring and for obtaining arterial blood samples, and a triple lumen pulmonary artery catheter was placed percutaneously in the jugular vein for obtaining mixed venous blood and to measure central venous and pulmonary artery pressures. ECG, pulse oximetry, end-tidal carbon dioxide and inhaled anesthetic concentration were continuously monitored. After obtaining baseline hemodynamic and metabolic measurements (blood gases, lactates and cyanide levels), the rabbits received a continuous infusion of sodium cyanide to induce CN toxicity as described in the Borron model. Borron, S. W., et al., *Clin. Toxicol. (Phila.)* 2006, 44 Suppl 1, 5-15.

The antidote (a sulfanegenic acid salt) or placebo (phosphate buffered saline) was administered (im, gluteus muscle) 2 minutes post apnea with death/survival as the primary endpoint. Return of blood cyanide and lactate to baseline levels served as secondary endpoints. The surviving NZW rabbit and Swiss-Webster mice were euthanized one week after recovery from anesthesia using an IACUC approved protocol.

Dose titration of the sulfanegen lysine/lysine HCl formulation in the mouse model (vide supra) revealed a steep dose response. A dose of this formulation equivalent to 81 mg/kg sulfanegenic acid resulted in greater than 93% survival, whereas half that dose gave only 40% survival and a dose equivalent to 20 mg/kg sulfanegenic acid resulted in 100% death (FIG. 1).

Figure 2:
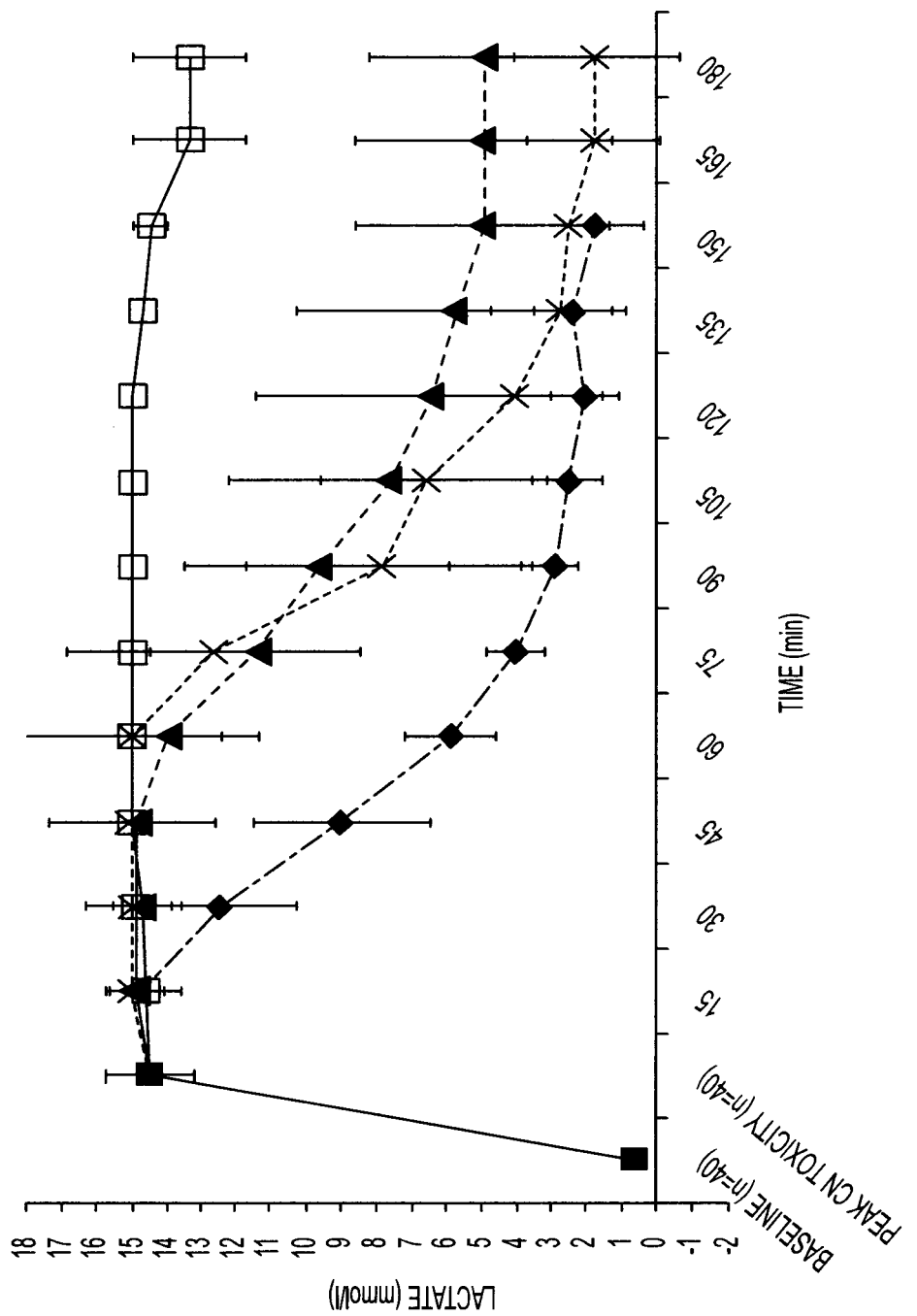
FIG. 2 shows the dose response of the sulfanegen lysine/lysine HCl formulation in the New Zealand white rabbit cyanide model. Dosages given are the amount of the free acid 2 delivered by the formulation. Lactate levels from 68 mg/kg dose (diamond), 51 mg/kg (X), 34 mg/kg (triangle) and 17 mg/kg (square) are shown. Placebo treated animals (not shown) died before the 15 minute time point

Dose titration of the sulfanegen lysine/lysine HCl formulation in the NZW rabbit also revealed a steep dose response. All animals receiving a dose of the formulation equivalent to 67 mg/kg sulfanegenic acid survived, whereas 50% of animals receiving half that dose survived and no animals survived at 17 mg/kg (Table 2). Not surprisingly, the 68 mg/kg dose gave the most rapid return of cyanide to the baseline (FIG. 2). All surviving animals appeared normal, displaying no neurological deficit by gross observation.

TABLE 2

Dose and survival in the New Zealand white rabbit lethal cyanide model.

| Dose (mg/kg) | n | Survival |
|---|---|---|
| 68 | 10 | 100% |
| 51 | 10 | 70% |
| 34 | 10 | 50% |
| 17 | 10 | 0% |
| 0 (placebo) | 10 | 0% |

Example 2

General Methods.

$^1$H and $^{13}$C NMR spectra were obtained on a Varian 600 MHz spectrometer in the Center for Drug Design, University of Minnesota, Minneapolis, Minn., except for the time studies which were performed on a Varian 200 MHz spectrometer. All chemical shifts are referenced to residual undeuterated solvent. Data of proton spectra are reported as follows: chemical shift (multiplicity [singlet (s), doublet (d), triplet (t), quartet (q) and multiplet (m)], coupling constants [Hz], and integration). Carbon spectra (150 MHz) were recorded with complete proton decoupling and the chemical shifts are reported in ppm (C) relative to solvent resonance as internal standard except those in $D_2O$ where $C_6D_6$ or $CD_3OD$ contained inside a coaxial insert was referenced as an external standard. X-Ray structure determinations were performed by Victor G. Young, Jr. of the X-Ray Crystallographic Laboratory, University of Minnesota, Minneapolis, Minn. Compound purity at 95% or greater was determined by microanalyses performed by Atlantic Microlab, Inc., Atlanta, Ga., or by MHW Laboratories, Phoenix Ariz. Unless stated otherwise, all the reagents were purchased from commercial sources and used without additional purification.

All studies involving animals (vide infra) were carried out according to NIH Guidelines for the Care and Use of Laboratory Animals and were approved by the University of Minnesota Institutional Animal Care and Use Committee (IACUC).

Mice were anesthetized with isoflurane to minimize pain and distress during cyanide exposure. Respiration of anesthetized animals was regular, albeit reduced in rate, and the animals did not require mechanical ventilation. Due to the rapid metabolism and large body surface-to-volume ratios of mice, hypothermia of anesthetized animals was a concern. To address this possibility, animals receiving parenteral cyanide were kept on a water-heated operating platform maintained at 36° C. In all experiments, surviving animals were observed for at least 24 h post experiment to determine if they manifested adverse effects from the cyanide or the drugs. Five or more animals were studied per dose of antidote.

The mice were anesthetized in an induction chamber with 3% isoflurane and 100% $O_2$, and then maintained on a nose-cone supply of 2% isoflurane in room air. Once the animals were anesthetized, 0.16 mmol/kg of potassium cyanide (KCN) dissolved in 10 mM sodium carbonate, pH 9.5 was injected into the peritoneal cavity. This is a fully lethal dose, and, in the absence of antidote, the following sequence of events occurs post cyanide injection: (i) animals become apneic within 1 min, i.e., all evidence of breathing ceases; (ii) after ~1 min of apnea, they develop agonal breathing characterized by diaphragmatic and chest muscle spasm; and (iii) after 1-4 min of agonal breathing, all respiratory activity ceases, and the animals are considered dead. The antidote dissolved in 0.1 ml sterile saline was injected into the gastrocnemius 60 seconds after the above cyanide injection. Control animals received 0.1 ml of intravenous saline 60 seconds after the cyanide injection.

The antidote was also evaluated in NZW rabbits using a method based on the Borron beagle dog model as follows (Borron, S. W.; Stonerook, M.; Reid, F., *Clin. Toxicol. (Phila.)* 2006, 44 Suppl 1, 5-15). After approval by our IACUC, NZW rabbits (3-5 kg) New Zealand white (NZW) rabbits were sedated (telazol, im) before general anesthesia with ketamine, and kept normocarbic and normothermic with a forced air warming device (Arizant Inc., Eden Prairie, Minn.). Monitoring included continuous EKG, pulse oximetry, skeletal muscle tissue $O_2$, $ETCO_2$, respiratory rate and core temperature. A percutaneously placed ear-lobe arterial line allowed for continuous monitoring of BP and blood sampling and a triple lumen pulmonary artery catheter was placed percutaneously in the jugular vein for obtaining mixed venous blood and to measure central venous and pulmonary artery pressures. ECG, pulse oximetry, end-tidal carbon dioxide and inhaled anesthetic concentration were continuously monitored. Cyanide toxicity in the spontaneously breathing animals was induced by the infusion of sodium cyanide via a peripheral iv infusion at 2.2 mg/kg/hr. Peak CN toxicity was defined as the occurrence of severe, significant lactic acidosis accompanied by hypopnea or apnea±hypotension. When this occurred, the NaCN infusion was stopped and the rabbits (n=10 per group) were immediately administered either antidote or placebo. All the animals that survived were metabolically tracked until their blood lactate concentration returned to the baseline, and hemodynamic stability was achieved. Necropsy was conducted in the animals that died during the experiment or within the 7-day period following the study. Survivors were euthanized by an IACUC approved protocol (overdose of anesthesia) one week after the study.

Procedure for the Preparation of 2,5-dihydroxy-1,4-dithiane-2,5-dicarboxylic acid (Sulfanegenic Acid, 2).

A solution of disodium 2,5-dihydroxy-1,4-dithiane-2,5-dicarboxylic acid tetrahydrate (0.25 g, 0.70 mmol) in $H_2O$ (2.5 mL) was applied to a column of ion-exchange resin Dowex 50WX8-200 ($H^+$; 7 eq), and was eluted with $H_2O$ until the eluate tested negative for the presence of dithiane by $KMnO_4$ stain on TLC silica plate. The resulting solution was then lyophilized to yield a white solid.

Procedure for Preparation of Metal Ion Salts (3b-3f):

A solution of disodium 2,5-dihydroxy-1,4-dithiane-2,5-dicarboxylic acid tetrahydrate (0.25 g, 0.70 mmol) in $H_2O$ (2.5 mL) was applied to a column of ion-exchange resin Dowex 50WX8-200 ($M^+$; 7 eq) where $M^+$ is the appropriate metal counterion), and was eluted with $H_2O$ until the eluate tested negative for the presence of dithiane by $KMnO_4$ stain on TLC silica plate. The resulting solution was then lyophilized to yield a white solid. NMR characterization of these salts was identical to that of the sodium salt (Nagasawa, H. T., et al., *J. Med. Chem.* 2007, 50, 6462-6464, Patterson, S. E., et al., *J. Med. Chem.* 2013, 56, 1346-1349).

Procedure for Preparation of Ammonium Salt (3e):

The ethylenediammonium salt 3e was prepared by addition of a 1.0 M solution of the desired amine (1 equiv.) in $H_2O$ to the solution obtained immediately upon eluting 2,5-dihydroxy-1,4-dithiane-2,5-dicarboxlic acid (2), followed by lyophilization to constant weight to yield white solids.

Procedure for Preparation of Ammonium Salts (3h-3Ee):

Sulfanegen salts 3h-3ee were prepared by addition of a 1.0 M solution of the desired amine (2 equiv.) in $H_2O$ to the solution obtained immediately upon eluting 2,5-dihydroxy-1,4-dithiane-2,5-dicarboxlic acid (2), followed by lyophilization to constant weight to yield white solids.

Characterization data for the metal and ammonium salts prepared via ion exchange chromatography are provided below.

Dilithium 2,5-Dihydroxy-1,4-dithiane-2,5-dicarboxylate (3b)

Anal. Calcd for $C_6H_6Li_2O_6S_2 \cdot 2½ H_2O$: C, 24.25; H, 3.73; S, 21.58. Found: C, 24.36; H, 3.64; S, 21.57.

Dipotassium 2,5-Dihydroxy-1,4-dithiane-2,5-dicarboxylate (3c)

Anal Calcd for $C_6H_6O_6S_2K_2 \cdot 2½ H_2O$: C, 19.94; H, 3.07; S, 17.74. Found: C, 19.97; H, 2.93; S, 17.53.

Dicesium 2,5-Dihydroxy-1,4-dithiane-2,5-dicarboxylate sesquihydrate (3d)

Anal Calcd for $C_6H_6O_6S_2Cs_2 \cdot 1½ H_2O$: C, 13.57; H, 1.71; S, 12.08. Found: C, 13.59 (13.55); H, 1.44 (1.47); S, 11.99.

2,5-Dihydroxy-1,4-dithiane-2,5-dicarboxylic acid, bis-ammonium salt (3e)

Anal Calcd for $C_6H_{14}N_2O_6S_2$: C, 26.27; H, 5.14; N, 10.21; S, 23.38. Found: C, 26.32; H, 4.86; N, 9.92; S, 23.61.

Calcium 2,5-Dihydroxy-1,4-dithiane-2,5-dicarboxylate sesquihydrate (3f)

$C_6H_6O_6S_2Ca \cdot 1½H_2O$. Calculated: C, 23.60; H, 2.97; S, 21.00. Found: C, 23.41 (23.54); H, 2.78 (2.84); S, 20.86.

2,5-Dihydroxy-1,4-dithiane-2,5-dicarboxylic acid, ethylenediamine salt hemihydrate (3g)

NMR ($D_2O$): δ 2.86 (d, 2H), 3.39 (s, 4H), 3.87 (d, 2H). $^{13}C$ NMR ($C_6D_6$): δ 36.8, 37.3, 77.9, 177.7. Anal Calcd for $C_8H_{16}N_2O_6S_2 \cdot ½H_2O$: C: 31.06; H: 5.54; N: 9.06; S: 20.73. Found: C: 31.35 (31.28); H: 5.63; N: 9.18 (9.07); S: 20.96.

2,5-Dihydroxy-1,4-dithiane-2,5-dicarboxylic acid, bis-diethylamine salt (3h)

$^1H$ NMR ($D_2O$): δ 1.29 (t, 12H), 2.87 (d, 2H), 3.09 (q, 8H), 3.87 (d, 2H). $^{13}C$ NMR ($CD_3OD$): δ 11.4, 36.9, 43.1, 77.9, 177.7. Anal Calcd for $C_{14}H_{30}N_2O_6S_2$: C: 43.50; H: 7.82; N: 7.25; S: 16.59.

Found: C: 43.71; H: 8.00; N: 7.32; S: 16.75.

2,5-Dihydroxy-1,4-dithiane-2,5-dicarboxylic acid, bis-L-histidine salt monohydrate (3i)

$^1H$ NMR ($D_2O$): δ 2.88 (d, 2H), 3.36 (m, 4H), 3.87 (d, 2H), 4.04 (m, 2H), 7.41 (s, 2H), 8.68 (s, 2H). $^{13}C$ NMR ($C_6D_6$): δ 26.5, 36.6, 54.3, 77.8, 118.4, 134.7, 173.3, 177.6. Anal. Calcd for $C_{18}H_{26}N_6O_{10}S_2 \cdot H_2O$: C: 38.02; H: 4.96; N, 14.78; S, 11.28. Found: C, 37.88; H, 4.96; N, 14.44; S, 11.15.

2,5-Dihydroxy-1,4-dithiane-2,5-dicarboxylic acid, bis-D-lysine salt sesquihydrate (3j)

$^1H$ NMR ($D_2O$): δ 1.47-1.57 (m, 4H), 1.92 (m, 4H), 2.89 (d, 2H), 3.05 (t, 4H), 3.79 (t, 2H), 3.88 (d, 2H). $^{13}C$ ($C_6D_6$):

δ 22.1, 27.1, 30.6, 36.6, 39.8, 55.2, 77.7, 175.2, 177.5. Anal Calcd for $C_{18}H_{36}N_4O_{10}S_2 \cdot 1.5\ H_2O$: C, 38.63; H, 7.02; N, 10.01; S, 11.46. Found: C, 38.40; H, 6.88; N, 9.57; S, 11.86.

2,5-Dihydroxy-1,4-dithiane-2,5-dicarboxylic acid, bis-L-lysine salt monohydrate (3k)

$^1$H NMR (D$_2$O): δ 1.44-1.56 (m, 2H) 1.76 (m, 4H), 1.94 (m, 4H), 2.87 (d, 2H), 3.05 (t, 4H), 3.80 (t, 2H), 3.88 (d, 2H). $^{13}$C (C$_6$D$_6$): δ 22.1, 27.1, 30.6, 36.6, 39.8, 55.2, 77.7, 175.2, 177.5. Anal Calcd for $C_{18}H_{36}N_4O_{10}S_2 \cdot H_2O$: C, 39.26; H, 6.96; N, 10.17; S, 11.65. Found: C, 39.12; H, 6.79; N, 10.07; S, 11.82.

2,5-Dihydroxy-1,4-dithiane-2,5-dicarboxylic acid, bis-L-aspartate salt (3l)

$^1$H NMR (D$_2$O): δ 2.98 (d, 2H), 3.08 (t, 4H), 3.91 (d 2H), 4.21 (t, 2H). $^{13}$C NMR (C$_6$D$_6$): δ 34.9, 35.7, 50.8, 76.6, 172.8, 174.4, 175.7. Anal Calcd for $C_{15}H_{22}N_2O_{14}S_2$: C, 33.20; H, 4.38; N, 5.53; S, 12.66. Found: C, 32.92; H, 4.41; N, 5.40; S, 12.55.

2,5-Dihydroxy-1,4-dithiane-2,5-dicarboxylic acid, bis-L-glutamate salt dodanhydrate (3m)

$^1$H NMR (D$_2$O): δ 2.22 (m, 4H), 2.64 (m, 4H), 2.97 (d 2H), 3.91 (d, 2H), 3.96 (t, 2H). $^{13}$C NMR (C$_6$D$_6$): δ 25.9, 30.4, 35.8, 37.8, 53.8, 76.7, 173.6, 175.9, 177.3. Anal Calcd for $C_{16}H_{26}N_2O_{14}S_2 \cdot \frac{3}{4}H_2O$: C, 35.07; H, 5.06; N, 5.11; S, 11.70. Found: C, 35.08; H, 4.96; N, 5.05; S, 11.54.

2,5-Dihydroxy-1,4-dithiane-2,5-dicarboxylic acid, bis-L-serine salt monohydrate (3n)

$^1$H NMR (D$_2$O): S 2.97 (d, 2H), 3.90 (d, 2H), 4.03 (m, 6H). $^{13}$C NMR (C$_6$D$_6$) δ 35.8, 37.8, 56.3, 60.5, 76.7, 172.1, 176.0. Anal Cacld for $C_{12}H_{22}N_2O_{12}S_2 \cdot H_2O$: C, 30.77; H, 5.16; N, 5.98; S, 13.69. Found: C, 30.78; H, 5.23; N, 5.81; S, 13.80.

2,5-Dihydroxy-1,4-dithiane-2,5-dicarboxylic acid, bis-L-threonine salt monohydrate (3o)

$^1$H NMR (D$_2$O): δ 1.36 (d, 6H), 2.96 (d, 2H), 3.80 (d, 2H), 3.90 (d, 2H), 4.35 (t, 2H). $^{13}$C (C$_6$D$_6$): δ 19.9, 35.8, 37.8, 60.2, 66.3, 76.7, 172.4, 175.9. Anal Calcd for $C_{14}H_{26}N_2O_{12}S_2 \cdot H_2O$: C, 33.87; H, 5.68; N, 5.64; S, 12.92. Found: C, 34.01; H, 5.63; N, 5.58; S, 13.30.

2,5-Dihydroxy-1,4-dithiane-2,5-dicarboxylic acid, bis-L-asparagine salt monohydrate (3p)

$^1$H NMR (D$_2$O): δ 2.96 (m, 4H), 2.98 (d, 2H), 3.91 (d, 2H), 4.18 (m, 2H). $^{13}$C NMR (C$_6$D$_6$): δ 34.9, 35.8, 51.2, 76.7, 173.0, 174.7, 175.9. Anal Calcd for $C_{14}H_{24}N_4O_{12}S_2 \cdot H_2O$: C, 32.18; H, 5.02; N, 10.72; S, 12.27. Found: C, 32.35; H, 4.69; N, 10.50; S, 12.62.

2,5-Dihydroxy-1,4-dithiane-2,5-dicarboxylic acid, bis-L-glutamine salt monohydrate (3q)

$^1$H NMR (D$_2$O): δ 2.21 (m, 4H), 2.51 (m, 4H), 2.97 (d, 2H), 3.91 (d, 2l), 3.94 (m, 2H). $^{13}$C NMR (C$_6$D$_6$): δ 26.6, 31.4, 35.9, 54.1, 76.8, 173.7, 176.0, 178.1. Anal Calcd for $C_{16}H_{28}N_4O_{12}S_2 \cdot H_2O$: C, 34.90; H, 5.49; N, 10.18; S, 11.65. Found: C, 35.13; H, 5.62; N, 10.34; S, 11.50.

2,5-Dihydroxy-1,4-dithiane-2,5-dicarboxylic acid, bis-L-glycine salt hemihydrate (3r)

$^1$H (D$_2$O): δ 2.95 (d, 2H), 3.73 (s, 4H), 3.90 (d, 2H). $^{13}$C (C$_6$D$_6$): δ 35.9, 41.4, 76.8, 171.8, 176.1. Anal Calcd for $C_{10}H_{18}N_2O_{10}S_2 \cdot \frac{1}{2}H_2O$: C, 30.07; H, 4.79; N, 7.01; S, 16.06. Found: C, 29.88; H, 4.77; N, 6.54; S, 16.40.

2,5-Dihydroxy-1,4-dithiane-2,5-dicarboxylic acid, bis-L-proline salt tetartohydrate (3s)

$^1$H NMR (D$_2$O): δ 2.06 □m, 4H), 2.15 (m, 2H), 2.40 (m, 2H), 2.97 (d, 2H), 3.38 (m, 2H), 3.44 (m, 2H), 3.90 (d, 2H), 4.26 (m, 2H). $^{13}$C NMR (C$_6$D$_6$): δ 24.3, 29.4, 35.8, 46.9, 61.3, 76.6, 174.3, 175.8. $C_{16}H_{26}N_2O_{10}S_2 \cdot \frac{1}{4}H_2O$. Calculated: C, 40.46; H, 5.62; N, 5.90; S, 13.50. Found: C, 40.34; H, 5.55; N, 5.78; S, 13.81.

2,5-Dihydroxy-1,4-dithiane-2,5-dicarboxylic acid, bis-L-alanine salt (3t).

$^1$H NMR (D$_2$O): δ 1.54 (s, 6H), 2.95 (d, 2H), 3.90 (d, 2H), 3.98 (m, 2H). $^{13}$C NMR (C$_6$D$_6$): δ 16.4, 35.9, 50.3, 76.8, 174.6, 176.1. Anal Calcd for $C_{12}H_{22}N_2O_{10}S_2$: C, 34.44; H, 5.30; N, 6.69; S, 15.33. Found: C, 34.13; H, 5.38; N, 6.49; S, 15.03.

2,5-Dihydroxy-1,4-dithiane-2,5-dicarboxylic acid, bis-L-valine salt monohydrate (3u)

$^1$H NMR (D$_2$O): δ 1.05 (m, 12H), 2.34 (m, 2H), 2.95 (d, 2H), 3.79 (s, 2H), 3.90 (d, 2H). $^{13}$C NMR (C$_6$D$_6$): δ 17.4, 18.4, 35.9, 37.9, 60.1, 76.8, 173.7, 176.1 Anal Calcd for $C_{16}H_{30}N_2O_{10}S_2 \cdot H_2O$: C, 39.01; H, 6.55; N, 5.69; S, 13.02. Found: C, 39.17; H, 6.57; N, 5.56; S, 13.27.

2,5-Dihydroxy-1,4-dithiane-2,5-dicarboxylic acid, bis-L-isoleucine salt triatetarto hydrate (3v)

$^1$H NMR (D$_2$O): δ 0.97 (m, 6H), 1.04 (m, 6H), 1.33 (m, 2H), 1.51 (m, 2H), 2.04 (m, 2H), 2.96 (d, 2H), 3.87 (s, 2H), 3.90 (d, 2H). $^{13}$C NMR (C$_6$D$_6$): δ 11.7, 15.1, 25.3, 35.9, 36.5, 59.2, 76.8, 173.6, 176.1. Anal Calcd for $C_{18}H_{34}N_2O_{10}S_2 \cdot \frac{3}{4}H_2O$: C, 41.89; H, 6.93; N, 5.43; S, 12.43. Found: C, 41.83; H, 6.61; N, 5.38; S, 12.75.

2,5-Dihydroxy-1,4-dithiane-2,5-dicarboxylic acid, bis-L-leucine salt hemihydrate (3w)

$^1$H NMR (D$_2$O): δ 0.98 (s, 12H), 1.71-1.82 (m, 6H), 2.95 (d, 2H), 3.89 (s, 2H), 3.92 (d, 2H). $^{13}$C (C$_6$D$_6$): δ 21.6, 22.5, 24.8, 35.9, 37.9, 40.1, 53.2, 76.8, 174.9, 176.1 Anal Calcd for $C_{18}H_{34}N_2O_{10}S_2 \cdot \frac{1}{2}H_2O$: C, 42.26; H, 6.90; N, 5.48; S, 12.53. Found: C, 42.08; H, 6.81; N, 5.57; S, 12.66.

2,5-Dihydroxy-1,4-dithiane-2,5-dicarboxylic acid, bis-L-methionine salt monohydrate (3x)

$^1$H (D$_2$O): δ 2.16 (s, 6H) 2.20 (m, 2H) 2.28 (m, 2H), 2.67 (m, 4H), 2.96 (d, 2H), 3.91 (d, 2H), 4.04 (m, 2H). $^{13}$C (C$_6$D$_6$): δ 14.6, 29.4, 30.0, 35.9, 37.8, 53.7, 76.8, 79.2, 173.8, 176.0. Anal Calcd for $C_{16}H_{30}N_2O_{10}S_4 \cdot H_2O$: C, 34.52; H, 5.79; N, 5.03; S, 23.04. Found: C, 34.50; H, 5.67; N, 5.04; S, 23.28.

2,5-Dihydroxy-1,4-dithiane-2,5-dicarboxylic acid, bis-L-phenylananine salt (3y)

$^1$H NMR (D$_2$O): δ 1.44-1.56 (m, 4H) 3.19 (m, 2H) 3.34 (m, 2H), 3.90 (d, 2H), 4.13 (m, 2H), 7.35 (m, 4H), 7.41 (m, 2H), 7.45 (m, 4H). $^{13}$C (C$_6$D$_6$): δ 35.9, 36.7, 55.9, 76.8, 135.3, 173.5, 175.9. Anal Calcd for $C_{15}H_{30}N_2O_{10}S_2$: C, 38.95; H, 6.54; N, 6.06; S, 13.86. Found: C, 38.72; H, 6.34; N, 5.94; S, 13.58.

2,5-Dihydroxy-1,4-dithiane-2,5-dicarboxylic acid, bis-L-tryptophan salt monohydrate (3z)

$^1$H NMR (D$_2$O): δ 2.92 (d, 2H), 3.37 (m, 2H), 3.51 (m, 2H), 3.88 (d, 2H), 4.22 (m, 2H), 7.20 (m, 2H), 7.28 (m, 4H), 7.55 (s, 2H), 7.72 (s, 2H). $^{13}$C NMR (C$_6$D$_6$): δ 26.8, 35.9, 54.9, 76.8, 107.6, 112.7, 119.0, 120.2, 122.9, 125.9, 127.3, 137.0, 173.9, 176.0. Anal Calcd for $C_{28}H_{32}N_4O_{10}S_2 \cdot H_2O$: C, 50.44; H, 5.14; N, 8.40; S, 9.62. Found: C, 50.20 (50.16); H, 5.13 (5.15); N, 8.25 (8.24); S, 10.00.

2,5-Dihydroxy-1,4-dithiane-2,5-dicarboxylic acid, bis-creatine salt (3aa)

$^1$H NMR (D$_2$O): δ 2.93 (d, 2H), 3.07 (s, 6H), 3.89 (d, 2H), 4.10 (s, 4H). $^{13}$C NMR (C$_6$D$_6$): δ 36.11, 37.74, 53.48, 173.98. Anal Calcd for $C_{14}H_{26}N_6O_{10}S_2$. C, 33.46; H, 5.21; N, 16.72; S, 12.76. Found: C, 33.35; H, 5.28; N, 16.47; S, 12.53.

2,5-Dihydroxy-1,4-dithiane-2,5-dicarboxylic acid, bis-L-carnitine salt (3bb)

$^1$H NMR (D$_2$O): δ 2.58-2.66 (m, 4H), 2.88 (d, 2H), 3.24 (s, 18H), 3.46-3.52 (m, 4H), 3.88 (d, 2H), 4.67 (m, 2H). $^{13}$C NMR (C$_6$D$_6$): δ 36.53, 41.36, 54.88, 63.85, 70.48, 77.56, 175.73, 177.24. Anal Calcd for $C_{20}H_{38}N_2O_{12}S_2$: C, 42.69; H, 6.81; N, 4.98; S, 11.40. Found: C, 42.83; H, 6.78; N, 5.03; S, 11.14.

2,5-Dihydroxy-1,4-dithiane-2,5-dicarboxylic acid, bis-L-ornithine salt dihydrate (3cc)

$^1$H NMR (D$_2$O): δ 1.72-1.99 (m, 8H), 2.87 (d, 2H), 3.07 (t, 4H), 3.80 (t, 2H), 3.87 (d, 2H). $^{13}$C NMR (C$_6$D$_6$): δ 36.53, 41.36, 54.88, 63.85, 70.48, 77.56, 175.73, 177.24. Anal Calcd for $C_{16}H_{32}N_4O_{10}S_2 \cdot 2H_2O$: C, 35.55; H, 6.71; N, 10.36; S, 11.86. Found: C, 35.81; H, 6.40; N, 10.37; S, 11.83.

2,5-Dihydroxy-1,4-dithiane-2,5-dicarboxylic acid, bis-(2,3-diaminopropionic acid) salt monohydrate (3dd)

$^1$H NMR (D$_2$O): δ 2.86 (d, 2H), 3.48 (d, 4H), 3.87 (d, 2H), 4.02 (t, 2H). $^{13}$C NMR (C$_6$D$_6$): δ 36.31, 39.19, 50.69, 77.43, 171.39, 177.25. Anal Calcd for $C_{12}H_{24}N_4O_{10}S_2 \cdot H_2O$: C, 30.90; H, 5.62; N, 12.01; S, 13.75. Found: C, 30.93; H, 5.53; N, 11.81; S, 13.93.

2,5-Dihydroxy-1,4-dithiane-2,5-dicarboxylic acid, bis-L-carnosine salt sesquihydrate (3ee)

$^1$H NMR (D$_2$O): δ 2.75 (m, 4H), 2.85 (d, 2H), 3.14 (m, 2H), 3.25 (m, 6H), 3.87 (d, 2H), 4.52 (m, 2H), 7.28 (s, 2H), 8.62 (s, 2H). $^{13}$C NMR (C$_6$D$_6$): δ 29.47, 34.28, 37.96, 38.35, 56.46, 79.45, 119.07, 132.01, 135.58, 174.03, 178.80. Anal Calcd for $C_{24}H_{36}N_8O_{12}S_2 \cdot 1.5\ H_2O$: C, 40.05; H, 5.46; N, 15.57; S, 8.91. Found: C, 39.81; H, 5.55; N, 15.35; S, 8.88.

2,5-Dihydroxy-1,4-dithiane-2,5-dicarboxylic acid, bis-L-arginine sesquihydrate 3(ff)

$^1$H NMR (D$_2$O): δ 1.62-1.78 (m, 4H), 1.93 (m, 4H), 2.85 (d, 2H), 3.25 (m, 4H), 3.78 (m, 2H), 3.87 (d, 2H). $^{13}$C NMR (C$_6$D$_6$): δ 24.7, 28.4, 36.8, 41.3, 55.2, 77.9, 175.2, 177.8. Anal Calcd for $C_{24}H_{36}N_8O_{12}S_2 \cdot 1.5\ H_2O$: C, 40.05; H, 5.46; N, 15.57; S, 8.91. Found: C, 39.81; H, 5.55; N, 15.35; S, 8.88.

2,5-Dihydroxy-1,4-dithiane-2,5-dicarboxylic acid, bis-(2,6-diaminopimelic acid) salt tetarto hydrate (3gg)

$^1$H NMR (D$_2$O): δ 1.46-1.64 (m, 4H), 1.87-2.01 (m, 8H), 2.93 (d, 2H), 3.84-3.87 (m, 4H), 3.89 (d, 2H). $^{13}$C (C$_6$D$_6$) NMR: δ 24.8, 33.2, 34.6, 42.1, 80.1, 155.4, 177.2. Anal Calcd for $C_{20}H_{36}N_4O_{14}S_2 \cdot \frac{3}{4}H_2O$: C, 37.88; H, 5.96; N, 8.83; S, 10.11. Found: C, 37.98 (37.90); H, 6.12 (6.02); N, 8.76 (8.68); S, 9.86.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A pharmaceutical composition comprising, sulfanegen lysine, lysine hydrochloride, and water.

2. The composition of claim 1 wherein the molar ratio of sulfanegenic acid:lysine is about 1:2.

3. The composition of claim 1 wherein the molar ratio of sulfanegenic acid:lysine:lysine hydrochloride is about 1:2:0.4.

4. The composition of claim 1, which is formulated for intramuscular administration.

5. The composition of claim 1, which is formulated for intravenous administration.

6. The composition of claim 1 having a pH of greater than about 4.

7. The composition of claim 1 having a pH of less than about 5.

8. The composition of claim 1, which is formulated for intraosseous administration.

9. A pharmaceutical composition prepared by combining sulfanegen lysine, lysine hydrochloride, and water.

10. A pharmaceutical composition prepared by combining sulfanegenic acid and a solution of lysine in water.

11. A pharmaceutical composition prepared by combining sulfanegenic acid and a solution prepared by combining water, lysine and lysine hydrochloride.

12. A pharmaceutical composition comprising sulfanegenic acid solid, lysine solid, and lysine hydrochloride solid.

13. A pharmaceutical composition prepared by combining sulfanegenic acid solid, lysine solid, and lysine hydrochloride solid.

14. A method comprising combining a) a solution prepared by combining water, lysine and lysine hydrochloride and b) sulfanegenic acid to provide a resulting solution.

15. The method of claim 14 further comprising administering the resulting solution to an animal.

16. The method of claim 15 wherein the resulting solution is administered to the animal at least 1 hour after combining.

17. The method of claim 15 wherein the resulting solution is administered to the animal at least 15 hours after combining.

18. A method comprising combining a) water and b) sulfanegenic acid solid, lysine solid, and lysine hydrochloride solid to provide a resulting solution.

19. A kit comprising a) a solution prepared by combining water, lysine and lysine hydrochloride; b) sulfanegenic acid solid; and instructions for combining the solution and the solid to provide a composition suitable for treating cyanide poisoning.

20. A kit comprising a) sulfanegenic acid solid, lysine solid, and lysine hydrochloride solid; and instructions for combining the sulfanegenic acid solid, lysine solid, and lysine hydrochloride solid with water to provide a composition suitable for treating cyanide poisoning.

21. A nanoparticle comprising sulfanegen lysine and lysine hydrochloride.

22. A nanoparticle suspension comprising a plurality of nanoparticles as described in claim 21.

23. A pharmaceutical composition comprising a plurality of nanoparticles as described in claim 21 and a pharmaceutically acceptable carrier.

* * * * *